US008162866B2

(12) United States Patent  (10) Patent No.: US 8,162,866 B2
Mazzarolo                   (45) Date of Patent:     Apr. 24, 2012

(54) NECK BRACE

(75) Inventor: Giovanni Mazzarolo, Coste di Maser (IT)

(73) Assignee: Alpinestars Research SRL, Coste Di Maser (TV) (IT)

( * ) Notice: Subject to any disclaimer, the term of this patent is extended or adjusted under 35 U.S.C. 154(b) by 243 days.

(21) Appl. No.: 12/529,254

(22) PCT Filed: Mar. 1, 2007

(86) PCT No.: PCT/IT2007/000152
§ 371 (c)(1),
(2), (4) Date: Aug. 31, 2009

(87) PCT Pub. No.: WO2008/105009
PCT Pub. Date: Sep. 4, 2008

(65) Prior Publication Data
US 2010/0121238 A1    May 13, 2010

(51) Int. Cl.
*A61F 5/00*    (2006.01)
(52) U.S. Cl. .................................................. 602/18
(58) Field of Classification Search .............. 602/19, 602/18, 17, 5, 1; 128/95.1, 97.1; 2/468, 2/127, 115, 69, 455, 410, 411, 414, 415
See application file for complete search history.

(56) References Cited

U.S. PATENT DOCUMENTS

| | | |
|---|---|---|
| 2,820,455 A | 12/1953 | Hall |
| 3,477,425 A | 11/1969 | Grassi |
| 3,495,272 A | 2/1970 | Tempelhof |
| 3,765,412 A | 10/1973 | Ommaya et al. |
| 3,855,631 A | 12/1974 | Ettinger |
| 3,878,561 A | 4/1975 | Winiecki |
| 4,274,161 A | 6/1981 | Littler |
| 4,319,362 A | 3/1982 | Ettinger |
| 4,449,251 A | 5/1984 | Gauthier |
| 4,501,023 A | 2/1985 | Bilberry |
| 4,502,471 A | 3/1985 | Owens |
| 4,821,339 A | 4/1989 | Fair |
| 4,854,306 A | 8/1989 | Pujals |
| 4,996,720 A | 3/1991 | Fair |
| 5,003,968 A | 4/1991 | Mars |
| 5,039,035 A | 8/1991 | Fitzpatrick |
| 5,133,084 A | 7/1992 | Martin |

(Continued)

FOREIGN PATENT DOCUMENTS

DE    27 17 712 A1    10/1978

(Continued)

OTHER PUBLICATIONS

"PCT International Search Report dated Nov. 15, 2007 for PCT/IT2007/000152, from which the instant application is based," 2 pgs.

(Continued)

*Primary Examiner* — Patricia Bianco
*Assistant Examiner* — Tarla Patel
(74) *Attorney, Agent, or Firm* — Fredrikson & Byron, P.A.

(57) ABSTRACT

A neck brace (10) having a collar member (12) to be arranged around a wearer's neck, and a rear member (14) extending from, the collar member (12) and to be abutted on the wearer's back. The brace further comprises releasable fastening means (74, 75, 88*a*, 88*b*, 92) for fastening the collar member to the rear member, such that the collar member and the rear member may also be detached.

17 Claims, 3 Drawing Sheets

U.S. PATENT DOCUMENTS

| | | | |
|---|---|---|---|
| 5,230,698 A | 7/1993 | Garth | |
| 5,411,471 A * | 5/1995 | Terrazas | 602/18 |
| 5,437,613 A | 8/1995 | Reggio et al. | |
| 5,517,699 A | 5/1996 | Abraham, II | |
| 5,531,669 A | 7/1996 | Varnau | |
| 5,546,609 A | 8/1996 | Rush, III | |
| 5,590,826 A | 1/1997 | Endo | |
| 6,058,517 A | 5/2000 | Hartunian | |
| 6,067,665 A | 5/2000 | DePalma et al. | |
| 6,494,854 B1 | 12/2002 | Visness et al. | |
| 6,729,643 B1 | 5/2004 | Bassick | |
| 7,041,073 B1 | 5/2006 | Patron | |
| 7,371,221 B1 * | 5/2008 | Baker | 602/18 |
| 2004/0167448 A1 | 8/2004 | Heffez | |
| 2007/0010771 A1 * | 1/2007 | Leatt | 602/18 |
| 2010/0056968 A1 | 3/2010 | Mazzarolo | |
| 2010/0235973 A1 | 9/2010 | Mazzarolo | |
| 2010/0251468 A1 | 10/2010 | Mazzarolo | |
| 2010/0263112 A1 | 10/2010 | Mazzarolo | |
| 2011/0004980 A1 | 1/2011 | Leatt et al. | |

FOREIGN PATENT DOCUMENTS

| | | |
|---|---|---|
| DE | 31 36 466 A1 | 4/1983 |
| DE | 295 21 373 U1 | 4/1997 |
| DE | 195 45 299 A1 | 6/1997 |
| DE | 200 06 084 U1 | 8/2001 |
| EP | 0043990 A1 | 1/1982 |
| EP | 0023115 B1 | 12/1985 |
| FR | 2534115 A1 | 4/1984 |
| FR | 2700746 | 7/1994 |
| FR | 2719747 | 11/1995 |
| GB | 2 126 485 A | 3/1984 |
| SL | 9600306 A | 4/1998 |
| WO | 9809545 A1 | 3/1998 |
| WO | 9938401 A1 | 8/1999 |
| WO | 0125088 | 4/2001 |
| WO | 02089620 A1 | 11/2002 |
| WO | 03077793 A2 | 9/2003 |
| WO | 03092561 | 11/2003 |
| WO | 2005051251 A | 6/2005 |
| WO | 2005107658 A | 11/2005 |

OTHER PUBLICATIONS

"PCT International Search Report dated Nov. 15, 2007 for PCT/IT2007/000153," 2 pgs.

English-language Abstract FR2534115 (Nolan SPA).

English-language Abstract FR2700746 (Schegerin).

English-language Abstract FR2719747 (Streiff Motorsport).

\* cited by examiner

US 8,162,866 B2

NECK BRACE

TITLE OF THE APPLICATION

CROSS-REFERENCE TO RELATED APPLICATIONS

This application is a US 371 national stage entry of International Application No. PCT/IT07/00152, filed Mar. 1, 2007.

BACKGROUND (1) Field of the Invention

The present invention relates to a neck brace used to enhance the protection given by a helmet to the head and neck of a wearer, particularly a rider in a sport activity, e.g. motor racing.

(2) Description of Related Art

It is nowadays compulsory for participant in such sport activities as motor racing to wear helmets in order to protect their heads in the event of an accident.

In order to assure an additional protection to the wearer the use of collars made of resilient material, typically stiff foam, placed between the wearer's upper body and the base of a helmet, has been proposed (see for instance U.S. Pat. No. 6,058,517). The goal is to limit to some degree the movement of the head in case of an impact by reducing the gap in which the helmet can move. However, these collars have a fixed shape and can be uncomfortable to wear due to a lack of customisation.

Other neck braces extend up to the chest and back of the wearer, to maximize the stability of the neck brace.

Accordingly U.S. Pat. No. 6,494,854 discloses a cervical collar made of two rigid parts, a frontal part and a rear part, fastenable together around the neck.

WO 2005 051 252 discloses a neck brace with a collar member and a back member. The collar member is hingedly detachable in two halves which open laterally for insertion of the neck therebetween, while the back member is fixed to one of the two halves. Neck braces of this type have the major drawbacks that they are difficult to adapt to one's body and are cumbersome to put on. Furthermore these braces are overly restrictive and do not easily co-operate with other items of protective clothing that the user may have to wear to partake in their sport.

BRIEF SUMMARY OF THE INVENTION

The main object of the present invention is to provide a neck brace capable to overcome some of the above-mentioned drawbacks.

This object is obtained by a neck brace having
a collar member to be arranged around a wearer's neck, and
a rear member extending from the collar member and to be abutted on the wearer's back,
characterized by further comprising releasable fastening means for fastening the collar member to the rear member, such that the collar member and the rear member may also be detached.

Preferably, the releasable fastening means comprise a single-action releasable fastening member, such that said fastening member is operable with a single action performed by the user in order to detach the collar member and the rear member. This enhances the wearability and the comfort of the brace.

Preferably, the collar member comprises two separated halves connected one another by a releasable fastening member, which can advantageously be the single-action releasable fastening member. This allows to quickly don the brace with simple and easy movements.

Preferably, the releasable fastening member is mounted to pivot said two halves, such that they are able to rotate about said releasable fastening member in order to be divaricated. This further allows to quickly don the brace with simple and easy movements.

Preferably, the releasable fastening member is a rotatable pin member with a transverse projection able to be locked in a corresponding receiving seat (the latter may be formed either in the collar member or the rear member).

As variants, the rotatable pin member is an isolated piece able to be mounted integral with a half of the collar member and the corresponding receiving seat is obtained in the rear member. In this case one half may have a polygonal recess in which a head comprised in the isolated pin member can be accommodated in a complementary way. This is a simple but effective way of coupling the rotatable pin member and the collar member. Otherwise the rotatable pin member may be permanently integral with a half of the collar member.

BRIEF DESCRIPTION OF THE SEVERAL VIEWS OF THE DRAWINGS

Further features and advantages of the invention will better appear from the following description of some embodiments thereof, with reference to the accompanying drawings, in which.

In the following, references with suffix "a" and "b" are to be understood to be equal or corresponding parts in the neck-brace.

DETAILED DESCRIPTION OF THE INVENTION

Figure 1:
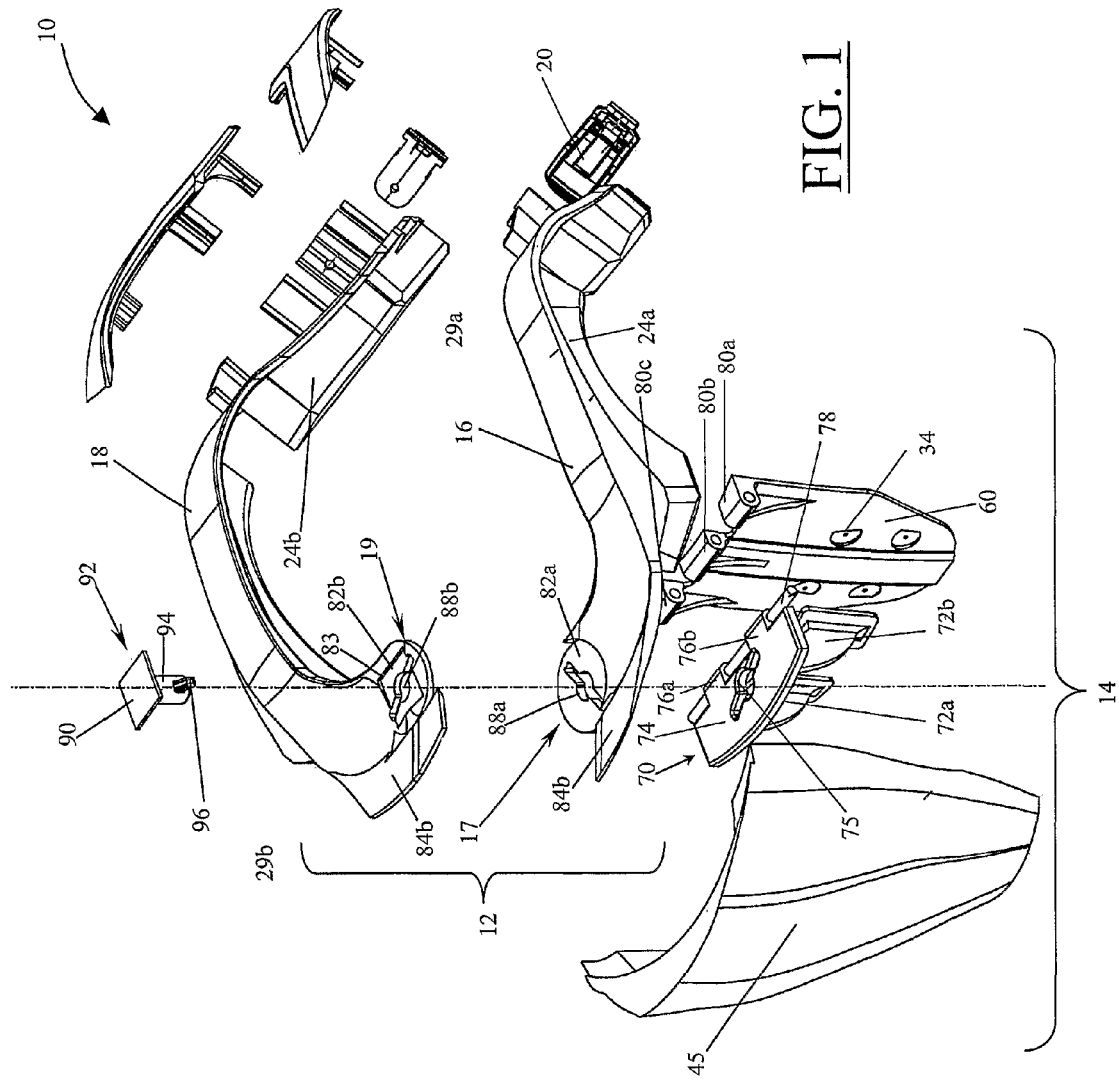
FIG. 1 shows an exploded view of the neck-brace parts.

With reference first to FIG. 1, a neck brace, generally indicated with reference 10, has a collar member 12, which, in use, extends around a wearer's neck, and a rear member 14, which, in use, rests upon the wearer's back.

The collar member 12 comprises two semi-circular halves 16, 18 which are frontally (i.e. at a wearer's chin) connected through closure means, e.g. a releasable buckle 20. The circular halves 16, 18 at the wearer's nape are jointed by releasable fastening means to each other and to the rear member 14, as more particularly described below.

The two halves 16, 18 have an upper surface 29a, b, which, in use, can abut against the lower surface of a helmet (not shown) and padded projections 24a, b which extend downwards from the collar member 12 at the shoulder and on the upper chest of the device. These projections 24a, b can be made of rigid material which would deform slightly under impact, e.g. high density expanded foams and the like, or softer materials, and are designed to rest, in use, on the wearer's shoulders and upper chest.

The two halves 16, 18 have a particular configuration in their rear section. Their rear ends 17, 19 are curved towards each other, rounded and end with a circular planar zone 82a, b rimmed with a lip 84a, b which projects outwards from the collar member 12. In the middle of each planar zone 82a, b there is a rectangular transverse slot 88a, b with a circular enlargement in the centre thereof (an overall shape resembling a key-hole). The planar zone 82b has a little deep squared (or generally polygonal) recess 83 on whose diagonal the slot 88b is obtained. The plant of the recess 83 corresponds to that of a plain head 90 comprised in a separated locking key 92 having a cylindrical body 94 with transverse projecting pins 96. The length of the pin 96 is the same as that of the slots 88a, b. Alternatively the locking key 92, instead of being an isolated piece, may be moulded permanently to the half 18 as well, eliminating the need for the zone 82b and the slot 88b.

The two rounded ends 17, 19 are shaped to be superimposed over each other and to be rotatable over one another. This thanks to the receiving planar zone 82a, which is the lower one and is slightly recessed to accommodate snugly the upper zone 82b. When two rounded ends 17, 19 are mounted superimposed the circular enlargements in the centre of the slots 88a, b line up. However, it is to be noted that, since the orientation of the slots 88a, b is not the same, namely they form different angles with respect to the longitudinal axes of the relative half part 16, 18 of the collar member 12, the slots 88a, b can line up only in a given open angular position of the halves 16, 18.

It is desired that when the halves 16, 18 are parallel (closed configuration for the collar member 12) the slots 88a, b do not line up, while they must line up when the halves 16, 18 are divaricated by a given amount (open configuration for the collar member 12).

How to use and wear the collar member 12 will be given hereunder.

The rear member 14 has a semi-elliptical base-plate 60 (made of plastic or metal material of any suitable type), with a plurality of openings 34 (only one indicated) which can cooperate with a plurality of studs onto the rider's garment to fix it thereupon. Velcro may be used as well for the fixing.

Figure 2:
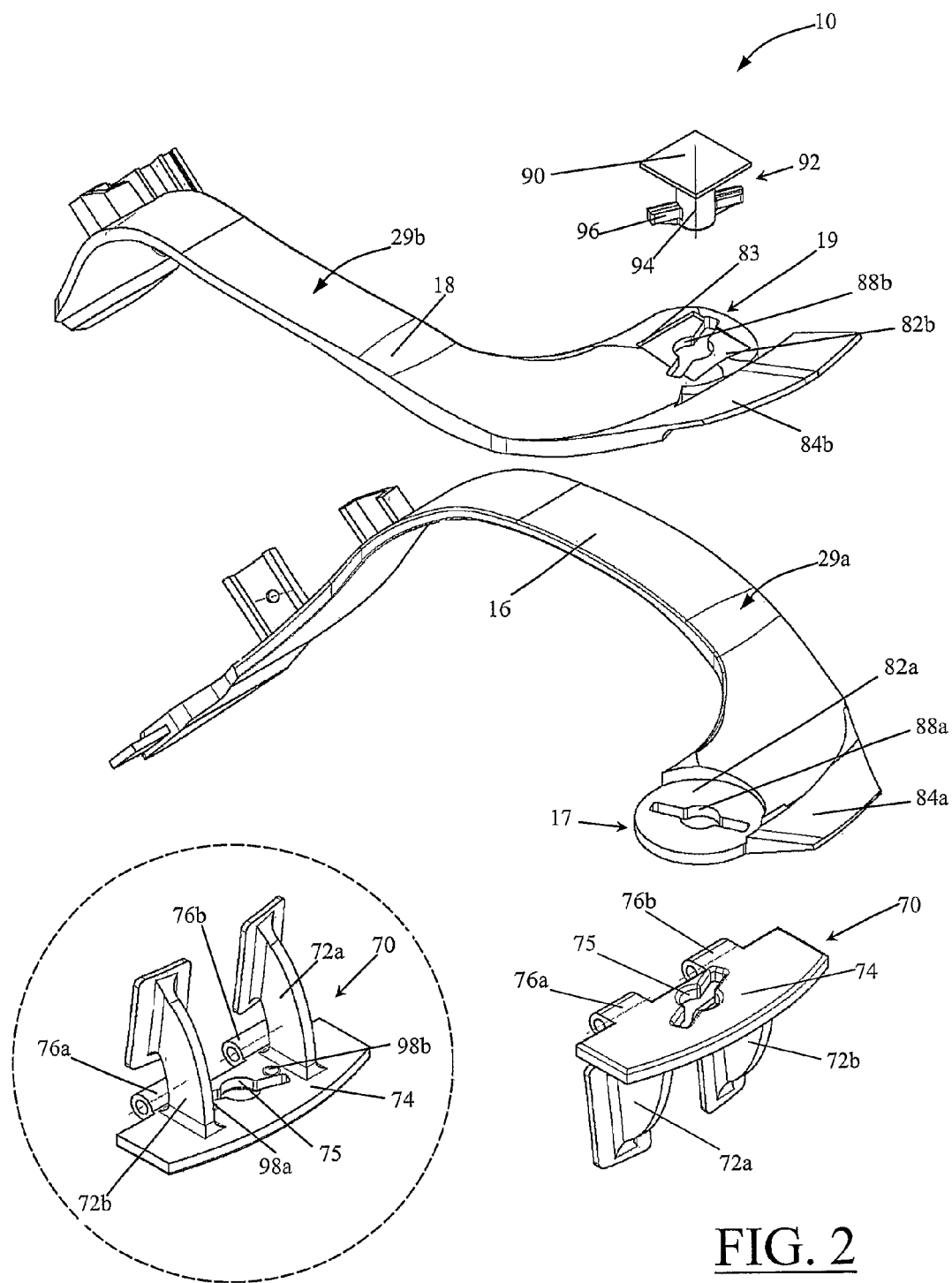
FIG. 2 shows a further exploded view of the principal base parts of the neck-brace in FIG. 1.
Figure 3:
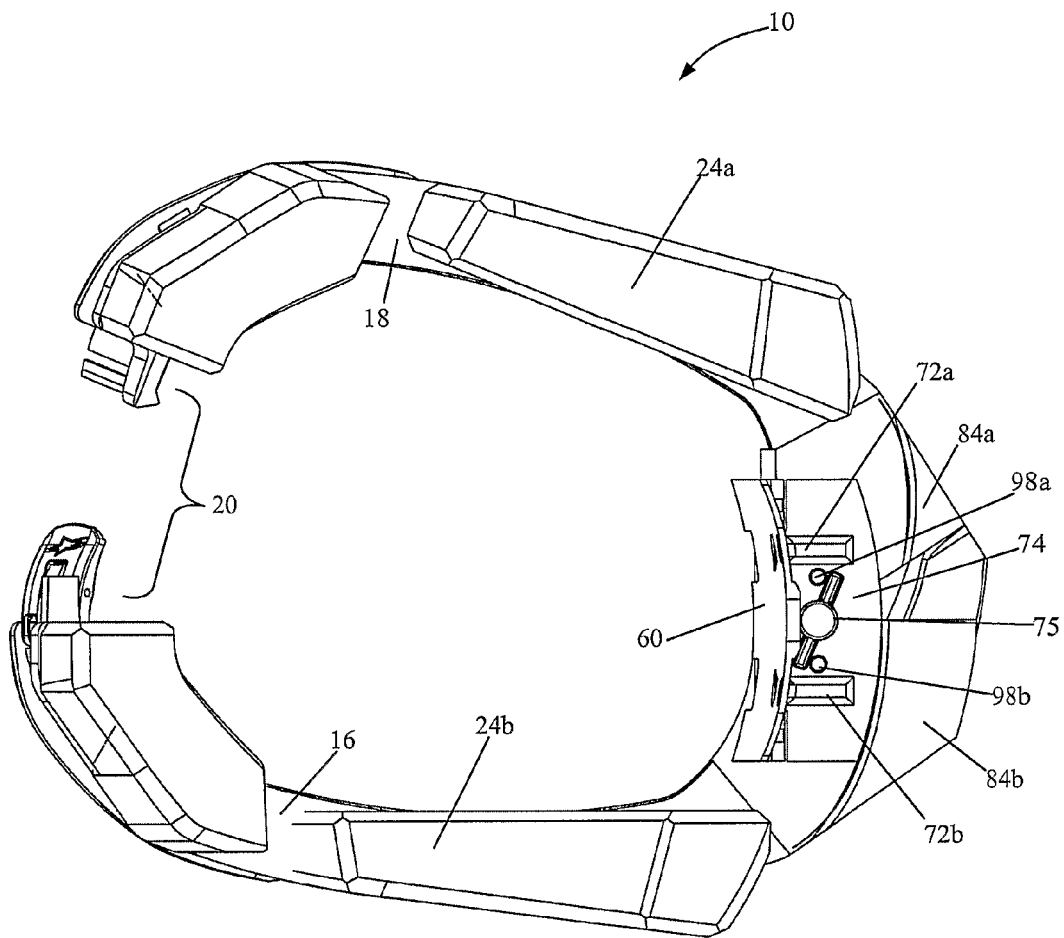
FIG. 3 shows a bottom view of the assembled neck-brace in FIG. 1.

To the base-plate 60, on which an aerodynamic hump 45 can be accommodated, there is hinged a support member 70 composed by two arched legs 72a, b and an upper plate 74. The legs 72a, b protrude from underneath the plate 74 and abut on the base-plate 60, while the upper plate 74 has two cylindrical bushes 76a, b provided on a border which are passed through by a pin 78. See the circle in broken lines of FIG. 2 for a botton view of the support 70.

The pin 78 also engages three bushes 80a, b, c on a border of the base-plate 60, thereby hinging the latter with the support member 70.

The upper plate 74 has a transverse slot 75, with dimensions equal to the slots 88a, b, but with different orientation with respect to them when the halves 16, 18 are parallel. Beside the slot 75, on the surface of the upper plate 74 facing the legs 72a, b, there are two lenticular dimples 98a, b.

The neck brace 10 can be worn as follows.

The plate 60 is attached to the rider's suit using stud fasteners and velcro, and the support member 70 is attached thereto using the pin 78. By abutting with the legs 72a, b against the edge of the plate 60 the support member 70 defines the amount of rearward freedom of the collar member 12 and it should be noted that by interchanging piece 70 with different dimension legs 72a, 72b the angle of the brace can be adjusted. Then for aerodynamic and styling purposes the padded hump 45 shape is attached to the back of the plate 60.

The locking key 92 is inserted in the slot 88b and its head 90 fitted in the complementary recess 83, thereby making it integrally rotatable with the half 18.

The two halves 16, 18 are then divaricated and superimposed in order to line up the slots 88a, 88b. Then the pin 96 of the locking key 92 is inserted into the slot 88a of the half 16 as well.

To don the collar member 12 the user then slides it over the neck from back to front. Without closing the halves 16, 18 the user then moves the collar member 12 down at the rear to engage the pin 96 in the slot 75 on the support element 70. At this point the user then rotates the halves 16, 18 to bring them near the neck, and fastens them with the frontal buckle 20. This single action causes the locking key 92, and hence the pin 96, to rotate on the underside of the support member 70. Thus the pin 96 jumps over the dimples 98a, b and stays secured on the other side thereof. This way the halves 16, 18 are coupled to the support member 70 (and hence to the garment of the rider) by means of the pin 96, which after rotation cannot escape form the slot 75.

To remove the collar member 12 the user opens the buckle 20, and separates the halves 16, 18. This will rotate the locking key 92 such that the pin 96 lines up with the slot 75, and the halves 16, 18 will be released therefrom. Once free from the support member 70, the halves 16, 18 may continue to be separated such that the pin 96 lines up with the slot 88a and the two halves 16, 18 can come apart. This reduces the overall size of the brace 10 and makes it easier for storage and transportation.

The invention claimed is:

1. A neck brace having a collar member to be arranged around a wearer's neck and a rear member extending from the collar member and to be abutted on the wearer's back, characterized by further comprising a single releasable fastening means for fastening the collar member to the rear member, such that the collar member and the rear member may also be detached, the collar member comprising two separated halves, the single releasable fastening means further connecting the two separated halves to one another.

2. The neck brace of claim 1 wherein the single releasable fastening means comprises a releasable fastening member.

3. The neck brace of claim 2 wherein the releasable fastening member comprises a single-action releasable fastening member, such that said single-action releasable fastening member is operable with a single action performed by a user in order to detach the collar member and the rear member.

4. The neck brace of claim 2 wherein said releasable fastening member is mounted to pivot said two halves such that they are able to rotate about said releasable fastening member in order to be divaricated.

5. The neck brace of claim 2 wherein the releasable fastening member is a rotatable pin member with a transverse projection able to be locked in a corresponding receiving seat.

6. The neck brace of claim 5 wherein the rotatable pin member is an isolated piece able to be mounted integral with one half of the collar member and the corresponding receiving seat is obtained in the rear member.

7. The neck brace of claim 6 wherein the one half has a polygonal recess in which a plain head comprised in the isolated pin member can be accommodated in a complementary way.

8. The neck brace of claim 5 wherein the rotatable pin member is permanently integral with one half of the collar member and the corresponding receiving seat is obtained in the rear member.

9. The neck brace of claim 5 wherein said halves in their rear ends are curved towards each other, and have a planar zone in which at least one of said halves has a pass-through slot in which the transverse projection can be inserted to reach the corresponding receiving seat in the rear member, said slot and the transverse projection being angularly oriented so as to line up through divarication of said halves from a closed configuration.

10. The neck brace of claim 5 wherein the rear member comprises a base-plate, on which an aerodynamic hump may be eventually accommodated, and a support member hinged thereto.

11. The neck brace of claim 10 wherein the base-plate comprises releasable fastening means for fastening it onto a rider's garment.

12. The neck brace of claim 11 wherein said releasable fastening means in the base-plate comprise a plurality of openings engageable in studs provided in the garment and/or strips of Velcro.

13. The neck brace of claim 10 wherein the support member comprises an upper plate in which a transverse slot is formed with dimensions adapted to engage said transverse projection.

14. The neck brace of claim 13 wherein said upper plate comprises protruding arched legs and abutting on the base-plate.

15. The neck brace of claim 13 wherein on the surface of the upper plate near its slot there are lenticular dimples able to lock in place the transverse projection.

16. The neck brace of claim 3 wherein the collar member is provided with a rear lip.

17. The neck brace of claim 16 wherein said rear lip comprises projecting rims which projects outwards from said halves.

* * * * *